United States Patent [19]

Rottig

[11] 4,199,523

[45] Apr. 22, 1980

[54] PROCESS FOR THE PRODUCTION OF HYDROCARBON MIXTURES

[75] Inventor: Walter Rottig, Oberhausen, Fed. Rep. of Germany

[73] Assignee: Ruhrchemie Aktiengesellschaft, Oberhausen, Fed. Rep. of Germany

[21] Appl. No.: 973,755

[22] Filed: Dec. 26, 1978

Related U.S. Application Data

[63] Continuation of Ser. No. 787,433, Apr. 14, 1977, abandoned, which is a continuation-in-part of Ser. No. 679,454, Apr. 22, 1976, abandoned.

[30] Foreign Application Priority Data

| | | | |
|---|---|---|---|
| Apr. 22, 1976 | [AU] | Australia | 13224/76 |
| Apr. 21, 1976 | [BE] | Belgium | 166342 |
| Apr. 22, 1976 | [CA] | Canada | 250791 |
| Apr. 22, 1976 | [DD] | German Democratic Rep. | 07192465 |
| Aug. 13, 1975 | [LU] | Luxembourg | 79509662 |

[51] Int. Cl.$^2$ .............................................. C07C 1/04
[52] U.S. Cl. .................... 260/449.6 R; 260/449.6 M; 260/449 R
[58] Field of Search ............... 260/449 S, 449.6 R, 260/449.6 M

[56] References Cited

FOREIGN PATENT DOCUMENTS 2518982 11/1976 Fed. Rep. of Germany ........ 260/449.6

*Primary Examiner*—Howard T. Mars
*Attorney, Agent, or Firm*—Bierman & Bierman

[57] ABSTRACT

There is disclosed a method for the production of hydrocarbon mixtures containing at least 50% by weight of $C_2$ to $C_4$ hydrocarbons and at least 50% by weight of olefins by catalytic hydrogenation of carbon monoxide in fixed-bed reactors under certain particular conditions which are necessary for the production of the aforementioned hydrocarbons.

21 Claims, No Drawings

PROCESS FOR THE PRODUCTION OF HYDROCARBON MIXTURES

This is a Rule 60 Continuation Application of Ser. No. 787,433 filed on Apr. 14th, 1977, abandoned; which is a Continuation-in-part application of Ser. No. 679,454 filed on Apr. 22nd, 1976, abandoned and which claims the priority of German Patent Applicaton P 25 18 982.6 filed Apr. 29th, 1975.

The catalytic hydrogenation of the oxides of carbon is broadly known. These prior art hydrogenation reactions produce mixtures of paraffins and olefins containing 1 to 40 carbon atoms and, in many cases, also produce oxygen containing compounds such as alcohols, aldehydes, ketones, esters, or fatty acids. Minor proportions of aromatic hydrocarbons are also produced under selected synthesis conditions (see Ullmann, Encyclopadie der technischen Chemie. 1957, Vol. 9, pp. 701 et seq.).

It has also been well-known that the elements of Group VIII of the Periodic Table are exceedingly active for the hydrogenation of the oxides of carbon. In particular, iron, cobalt, and nickel are useful in this reaction. Due to their high hydrogenation activity, nickel and cobalt catalysts yield predominantly mixtures of saturated, straight chain hydrocarbons. On the other hand, such catalysts based on iron permit the production of hydrocarbon mixtures containing high proportions of unsaturated aliphatic compounds. In addition, the iron base catalysts produce oxygen containing compounds, especially aliphatic primary alcohols (Ullmann, op. cit., pp. 697-698).

It is also easy to produce mixtures containing at least 60% by weight of hydrocarbons having more than about 20 carbon atoms. Such hydrocarbons would correspond to an atmospheric boiling range in excess of about 320° C. (see Ullmann, op. cit., pp. 722).

However, prior to the present invention, it was not possible to direct the hydrogenation reaction of the oxides of carbon to reaction products which contain more than 50% (by weight) of low molecular weight (preferably olefinic) hydrocarbons having 2 to 4 carbon atoms. The percentage set forth is based upon the total hydrocarbons having at least 2 carbon atoms.

It is therefore an object of this invention to provide a process for the preferential production of low molecular weight olefinic hydrocarbons by the catalytic reduction of oxides of carbon in the presence of hydrogen.

It has now been found that it is possible to produce hydrocarbon mixtures containing at least 50% by weight of $C_2$ to $C_4$ hydrocarbons and at least 50% by weight of olefins, all based on the total content of hydrocarbons having at least two carbon atoms, by the catalytic hydrogenation of the oxides of carbon in fixed-bed reactors under elevated temperature and pressure. These results can be achieved in a process in which the catalyst is arranged in at least 2 and not more than 10 layers in reactors having a length of about 0.5 to 4.5 meters. The synthesis pressure is about 5 to 30 bars, and the synthesis temperature is about 250° to 370° C., measured on the catalyst. The fresh gas load (or space velocity) is adjusted to about 1,000 to about 10,000 standard cubic meters per cubic meter of catalyst per hour. The gas recycle must be about 5 to 25 times the amount of fresh gas and the total gas load must be from about 7,500 to about 50,000 standard cubic meters per cubic meter of catalyst per hour. The catalyst is arranged so that the linear gas velocity is between about 1 and 10 meters per second, based on standard conditions. The residence time is between 0.05 and 1 second, based on standard conditions, and the catalyst used has an internal surface area of about 5 to 150 square meters per gram.

The catalysts are arranged in a fixed-bed in 2 to 10 layers. They may have the same or different grain sizes, but it is desirable that they be about 0.5 to about 10 millimeters and most preferred about 1 to 6 millimeters. The specific grain size is dependent upon various factors such as the activity of the catalyst, the diameter of the reactor, the resistance to flow and the operating conditions.

The shape of the catalyst is of minor importance. Cylindrical pellets, spherical pellets, tablets, polyhedra, and hollow bodies as well as lumpy, crushed and/or comminuted catalysts may all be used with good results.

The reactor may contain tubes having an inside diameter of, for example, a minimum of about 30 millimeters. These tubes may also be in bundles, or vessels such as shaft furnaces or similar apparatus may be used as fixed-bed reactors. The reactors may be provided with devices for cooling or removing the heat of reaction. In that event, cooling media such as water, liquid salt melts, or organic cooling liquids (based, for example, on biphenyl, o-dichlorobenzene or isomeric benzyl benzenes) may be used in the case of the tubes or tube bundles.

It is particularly advantageous to remove the heat of reaction almost completely by recycling the gas mixture. If necessary or desired, a cooling medium can also be used. When operating in this manner, the temperature in the catalyst bed is not uniform throughout, but increases in a controlled manner in the direction of the flow of the gas stream. Thus, the gas mixture enters the reactor at a temperature of, for example, 280° C. This temperature may increase as the gas flows through the reactor by about 50° C. to a temperature of 330° C. This is the result of absorption of part of the heat of reaction by the gas mixture. The temperature of the catalyst itself increases by approximately the same amount and the overall gas mixture leaves the reactor at this higher temperature. This increase in temperature (the vertical temperature gradient) should be at least 25° C. but should not exceed 100° C. The preferred vertical temperature gradient is 30° to 50° C.

In the preferred form of the reaction, the heat of reaction is removed by appropriately adjusting the gas recycle, without the use of a cooling medium. For technical and economic reasons, it is advisable to operate in a plurality of stages and to cool the reaction mixture partially or completely between the stages. If desired, the reaction products may be separated from the reaction liquor after each stage. The number of stages is approximately 2 to 10 and preferably 2 to 5.

In a variation of the present invention, cold fresh gas may be fed down stream of each of the aforementioned stages to partially cool the reaction mixture and to increase the proportion of carbon monoxide and hydrogen in the gas mixture. It is also possible, in this form of the reaction, to increase the reaction temperature from stage to stage to permit better control of the conversion of the carbon monoxide and hydrogen. This conversion decreases as the content of the starting materials in the reaction mixture goes down. This occurs, naturally, as a result of these materials being used up in the reaction itself. It has been found useful to increase the reaction temperature by about 5° to 20° C. from stage to stage.

The length of the reactors used to carry out the reaction must not exceed 4.5 meters. It is preferred to use reactors having a length of less than 3 meters. Reactors as short as 0.5 to 1.0 meters can be used without disadvantages in the present invention.

The pressure used is dependent upon the nature of the catalyst and ranges from 5 to 30 bars. More preferred are pressures between 5 and 15 bars. It has been noted that lower pressures frequently result in a decrease in the conversion of the starting materials.

The reaction temperatures are between 250° and 370° C., preferrably between 270° and 340° C.

It is of substantial importance for the proper operation of the present process that a high fresh gas load be maintained. In prior art fixed-bed catalyst reactions, a load of 500 to 700 standard cubic meters per cubic meter of catalyst per hour was generally considered to be the upper limit in the Fischer-Tropsch synthesis. Fresh gas rates greatly in excess of this "limit" are needed in the present invention. More specifically, it has been found desirable to supply 1,000 to 10,000 standard cubic meters of fresh gas per cubic meter of catalyst per hour. Preferably, 1,500 to 5,000 standard cubic meters of catalyst per hour are used.

In addition to the fresh gas load, the invention requires that the tail-gas be recycled. It is of particular importance that the ratio of the recycled gas to the fresh gas be maintained within certain limits. The recycled gas may be conducted through a plurality of stages before recycling but must be adjusted to about 5 to 25 times the amount of fresh gas introduced. It is most preferred that the ratio of recycled gas to fresh gas be from 7.5 to 15. In addition to the foregoing, the total gas load to the catalyst (the sum of the fresh gas and the recycle gas) must be between about 7,500 and about 50,000 standard cubic meters per cubic meter of catalyst per hour. The preferred total gas load being about 10,000 to 25,000 standard cubic meters of gas per cubic meter of catalyst per hour.

The linear flow velocity of the gas mixture and the residence time in the catalyst must also be controlled. Both of these variables are based on standard conditions and the linear gas flow velocity must be from 1 to 10 meters per second. The preferable range is 1.5 to 5.0 meters per second. The residence time is 0.05 to 1 second and the preferable range is from 0.05 to 0.5 seconds. It has been noted that the production of hydrocarbons of higher molecular weights is promoted by an increase in residence time.

The catalysts useful in the present invention are those normally used in the Fischer-Tropsch synthesis. These are generally known and are operable in the present process. However, it has been found that catalysts containing more than 50% by weight of iron are to be preferred. More preferred, are catalysts containing more than 60% by weight of iron. In addition, promoters such as copper and/or silver and alkali are desirable. Moreover, other additives such as alkaline earth metal compounds, zinc oxide, manganese oxide, cerium oxide, vanadium oxide, chromium oxide and the like may also be used. On the other hand, the use of support materials such as alumina, kieselguhr, or impregnating agents such as potassium or sodium water glass is less advantageous.

Boron, phosphorous, tungsten or molybdenum may be used as components of the catalyst in the form of their oxides or salts. Such salts as sodium borate or potassium tungstenate are recommended. It has been found particularly desirable to use catalysts based on iron, copper and/or silver and alkali ($K_2O$). More specifically, such a catalyst in a ratio of Fe:Cu/Ag:$K_2O$ of, for example, 100:3 to 25:10 has been found especially suitable.

The catalysts themselves may be produced in any known manner; for example, precipitation, sintering, fusion or decomposition of salt mixtures. Shaping, reduction, etc., of the catalysts may also be carried out in the known manner. In some cases, sintered catalysts have been found to be somewhat more advantageous.

The internal surface area of the catalysts is measured by the BET method and is important for the proper operation of the process of the present invention. Catalysts having an internal surface area in excess of 150 square meters per gram are likely to produce higher molecular weight hydrocarbons. Therefore, the catalysts used in the present process must have an internal surface area of about 5 to about 150 square meters per gram of catalyst. It is preferred that this range be about 10 to about 100 square meters per gram of catalyst. For those catalysts which contain predominant amounts of metals, especially iron, the internal surface area is bases on the reduced state.

It has been found that the pore size of the catalysts has a noticable influence on the proportion of low molecular weight hydrocarbons in the reaction product. The proportion of macropores having a diameter of more than about $5 \times 10^{-6}$ to $1 \times 10^{-5}$ centimeters bases on the total pore volume should be as low as possible since the macropores promote the production of the higher molecular weight hydrocarbons. Pores having a diameter is less than $5 \times 10^{-6}$ centimeters encourage the production of the lower molecular weight hydrocarbons. It is, therefore, advantageous if the catalysts used in the present process contain less than 50% macropores bases on the total pore volume. It is to be preferred that the catalysts contain less than 25% of the macropores.

It occasionally happens during the course of operation of the present process, that some of the catalyst pores become clogged by deposition of small amounts of high molecular weight reaction products. When this occurs, portions of the catalysts are no longer accessible to the synthesis gas. This condition evidences itself by a decrease in the conversion of carbon monoxide and hydrogen. The high molecular weight deposits may be removed by what is known as an extractive operation, i.e., extraction of the catalyst with hydrocarbon mixtures produced by the synthesis itself or with other hydrocarbon mixtures.

The catalysts may be produced in a manner known per se, e.g. by precipitation, sintering, fusion or decomposition of salt mixtures. Molding and reduction of the catalysts may also be effected in known manner. In some cases, sintered catalysts have been found to be advantageous The ratio of carbon monoxide to hydrogen in the fresh gas also has an influence on the production of low molecular weight hydrocarbons. While it is possible, in the present process, to use gases which are rich in carbon monoxide, it is preferred that the fresh gas be rich in hydrogen. The ratio of carbon monoxide to hydrogen in the fresh gas is preferably in excess of 1:1.2. It is most desired that the ratio be between 1:1.5 an 1:2. Higher proportions of hydrogen may be somewhat disadvantageous under certain circumstances.

The presence of inert gases such as methane, carbon dioxide, or nitrogen, generally does not interfere with the reaction. Since the proportion of this inert gases in the reaction mixture increases as the conversion of carbon monoxide and hydrogen increases due to the gas contraction which occurs, it is desirable to keep the inert gas concentration in the fresh gas low.

If the process is practiced in accordance with the present invention, it will yield more than 50% by weight and, in many cases, more than 60% by weight of hydrocarbons having 2 to 4 carbon atoms, based on the total amount of hydrocarbons excluding methane. The proportion of olefins is in excess of 50%, also based on the total hydrocarbons with the exclusion of methane.

EXAMPLE 1

A catalyst in the form of spherical pellets (about 2 to 2.5 millimeters in diameter) is prepared by sintering a homogeneous mixture of iron oxide (Alan Wood ore), copper oxide, zinc oxide, and potassium carbonate in the ratio of $Fe:Cu:ZnO:K_2O$ of 100:25:10:8 for 2 hours at 1050° C. The catalyst was reduced for several hours at 400° C. After termination of the treatment, the catalyst had a reduction value (percentage of free iron based on total iron) of 97%. The catalyst was placed in an electrically heated test reactor 1 meter in length and 50 millimeters in inside diameter. It formed a layer 50 centimeters in depth.

Fresh gas having the following composition:

| | | |
|---|---|---|
| $CO_2$ | 3.6% | by volume |
| $C_nH_m$ | 0% | by volume $N \geq 2$   $M = 2n$ |
| $O_2$ | 0% | by volume |
| CO | 30.7% | by volume |
| $H_2$ | 53.0% | by volume |
| $CH_4$ | 0.2% | by volume |
| $N_2$ | 12.5% | by volume |
| $CO/H_2$ ratio | 1:1.72 | | was introduced into the reactor at a rate of 2,000 standard liters per liter of catalyst per hour (2,000 v/v/hr.). Recycled gas was introduced at the rate of 15,000 standard liters per liter of catalyst per hour (15,000 v/v/hr.). The pressure was maintained at 10 atmospheres. A conversion of the carbon monoxide and hydrogen of 36% was obtained at a temperature of 260° C. measured outside of the catalyst, and at a temperature of 292° C. measured inside the catalyst.

The reaction mixture had the following composition based on hydrocarbons having 2 or more carbon atoms:

| | |
|---|---|
| $C_2/C_4$ | about 69.5% by weight; of these, 57% by weight were olefins; |
| $C_5$ to about $C_{11}$ | about 30.4% by weight; of these, 60% by weight were olefins. |

The proportion of methane was between 7 and 8% by weight.

The reaction mixture was conducted under pressure over activated carbon to remove the hydrocarbons which are gaseous standard conditions. The residual gas had the following composition:

| | |
|---|---|
| $CO_2$ | 9.9 vol. % |
| $C_nH_m$ | 0.7 vol. % |
| $O_2$ | 0 vol. % |
| CO | 22.8 vol. % |
| $H_2$ | 48.8 vol. % |
| $C_nH_{2n+2}$ | 1.4 vol. % |
| $N_2$ | 16.7 vol. % | which was then led to a second reaction step identical with the first. The operating conditions were the same except for the temperature which was 270° C. outside the catalyst and 291° C. inside the catalyst. A $CO/H_2$ conversion rate of about 34% was obtained.

The composition of the resulting reaction products with more than two C atoms was as follows: $C_2/C_4$ 71.1 wt.%, including 55% olefins; $C_5/$ and higher, 28.9% wt.%, including 57% olefins.

The proportion of newly formed methane was about 10 wt.%, based on all the hydrocarbons formed while the catalyst used corresponded to that of step 1.

EXAMPLE 2

The sintered catalyst was produced in accordance with Example 1 except that only 5 parts by weight of copper and 4 parts being weight of $K_2O$ were used. Otherwise, the conditions and composition were unchanged. The fresh gas and recycle gas rates were the same as in Example 1, but the reaction temperature was 270° C. outside of the catalyst and 313° C. inside the catalyst. As a result, the carbon monoxide and hydrogen conversion rate increased to about 40%. The composition of the synthesis products was as follows:

| | |
|---|---|
| $C_2/C_4$ | about 98% by weight |
| $>C_4$ | about 2% by weight |

The olefin content of the $C_2/C_4$ fraction was 56% by weight. The proportion of $C_2$ hydrocarbons in the $C_2/C_4$ fraction was about 90%, the balance being about equal amounts of $C_3$ and $C_4$ hydrocarbons. Methane in an amount of 10 to 12% by weight was also produced.

The synthesis gas used has the same composition as that set forth in Example 1.

After separation of the gaseous hydrocarbons under standard conditions, by means of activated carbon under pressure, the residual gas had the following composition:

| | |
|---|---|
| $CO_2$ | 10.2 vol. % |
| $C_nH_m$ | 0.4 vol. % |
| $O_2$ | 0 vol. % |
| CO | 22.1 vol. % |
| $H_2$ | 48.0 vol. % |
| $C_nH_{2n+2}$ | 1.9 vol. % |
| $N_2$ | 17.4 vol. % |

This gas was then reacted in a second reaction step comparable to the first, and under identical operating conditions except for the reaction temperatures of 280° C. outside the catalyst and 310° C. inside the catalyst. A 37% conversion of carbon monoxide and hydrogen was obtained.

The composition of the resulting products with more than two carbon atoms was as follows:

| | |
|---|---|
| C$_2$/C$_4$ | about 97 wt. % |
| C$_4$ | about 3 wt. % |

The percentage of the C$_2$ fraction in the C$_2$/C$_4$ hydrocarbons was about 85 wt.% while 8 wt.% consisted of C$_3$-, and 7 wt.% of C$_4$-hydrocarbons. The olfein content of the C$_2$-hydrocarbons was 53 wt.%, while the olefin content of the C$_3$-fraction was about 70 wt.% and about 65 wt.% for the C$_4$-fraction.

The methane formation was about 13% and the catalyst used corresponded to that of step 1.

EXAMPLE 3

Iron oxide (Alan Wood ore) was finely mixed with some copper oxide, zinc oxide and potassium carbonate and formed on a rotary plate to produce an spherical catalyst (2 to 3 mm diameter). The composition had a ratio of: 100 Fe: 2 Cu: 4 ZnO: 2 K$_2$O. The catalyst was sintered for three hours at 1100° C. and, after cooling reduced with hydrogen for several hours at 430° C.

Ten adjacent, serially connected, electrically heated reactors (clear width 60 mm, height 1.25 m) were filled with the above-prepared catalyst. The first stage contained 3.55 liters of catalyst. The amount of catalyst was decreased from stage to stage by about 5 percent by volume so that the tenth and last stage contained 1.8 liters of the catalyst.

After removal of the reaction gas from the first stage and subsequent cooling, the resulting C$_2$/C$_4$ hydrocarbons was separated from the reaction gas by passing said gas through an activated carbon layer under pressure. The hydrocarbons were removed from said activated carbon layer by contact with water vapor at a temperature of approximately 100° C. and about standard pressure by collecting said gaseous mixture in a gasometer. The remaining gas was then transferred to the second stage.

After passing into the second reaction and subsequent cooling, the recovery of the newly formed C$_2$/C$_4$ hydrocarbons took place as previously described. This process was carried out in the same manner for the third through the ninth reaction stage. The tenth and last reaction stage did not have the remaining gases pass through an activated carbon layer. Instead, the recovery of the C$_2$/C$_4$ hydrocarbons took place by means of cooling at a temperature of minus 60° C. wherein condensation of the desired hydrocarbons was effected.

The reaction temperatures, measured inside the catalyst, were between about 310° C. (first stage) and about 345° C. (last stage). Thus, the reaction temperature was increased from stage to stage by about 5° C.

Each stage was provided with recycled gas. The quantity of the recycled gas amounted to about six times the feed gas entering the single reactor. 2,500 standard liters per liter of catalyst per hour (2,500 v/vhr) of a synthesis gas with the following composition were passed from the first stage at a pressure of 11 bars:

| | % by volume |
|---|---|
| CO$_2$ | — |
| CO | 44 |
| H$_2$ | 55 |
| CH$_4$ | — |
| N$_2$ | 1 |

The carbon monoxide and hydrogen conversion in each stage amounted to about 20 percent based on the portion of these gases present in the inlet gas before each stage and after separation of the C$_2$/C$_4$ hydrocarbons.

Based on the procedure of the foregoing example, a total carbon monoxide and hydrogen conversion rate of 89.1% was attained based on a ten stage reaction. The composition of the thus formed synthesis products per Nm$^3$ of fed synthesis gas was as follows:

| | | |
|---|---|---|
| CH$_4$ | 15.8 grams | |
| C$_2$ hydrocarbons | 145.2 grams - | 55% by weight were olefins |
| C$_3$ hydrocarbons | 6.4 grams - | 65% by weight were olefins |
| C$_4$ hydrocarbons | 8.0 grams - | 60% by weight were olefins |
| C$_5$ and higher hydrocarbons | trace amounts | |

While only limited number of embodiments of the present process have been specifically described, the invention is, nonetheless, to be broadly construed and not to be limited except by the character of the claims appended hereto.

What is claimed is:

1. In a process for the production of hydrocarbon mixtures by catalytic conversion of gas comprising carbon monoxide and hydrogen in fixed bed reactors at elevated temperatures and under superatmospheric pressure wherein said catalyst is arranged in from 2 to 10 layers in said reactors, the improvement which comprises,
   (a) said reactors having a length of 0.5 to 4.5 meters,
   (b) said pressure being 5 to 30 bars,
   (c) said temperature being 250° to 370° measured in said catalyst,
   (d) introducing fresh gas at a space velocity of about 1,000 to about 10,000 standard m$^3$ per m$^3$ of said catalyst per hour,
   (e) recycling gas after contact with said catalyst, said recycle gas being introduced at a rate of about 5 to 25 times said space velocity,
   (f) said fresh gas and said recycle gas constituting a total gas load, said total gas load being about 7,500 to about 50,000 standard m$^3$ per m$^3$ of said catalyst per hour,
   (g) the linear velocity of said gas being from about 1 to 10 meters per second, based on standard conditions,
   (h) the residence time of said total gas load in said catalyst being 0.5 to 1 second, based on standard conditions, and
   (i) said catalyst having an internal surface area of about 5 to 150 m$^2$ per gram of said catalyst, whereby said mixtures contain at least 50% by weight of C$_2$ to C$_4$ hydrocarbons, based on the total weight of hydrocarbons having at least two carbon atoms, and at least 50% by weight of olefins based on the total weight of hydrocarbons having at least two carbon atoms.

2. A process according to claim 1 wherein the length of said reactor is less than 3 meters.

3. A process according to claim 1 wherein said pressure is 5 to 15 bar.

4. A process according to claim 1 wherein said temperature ist 270° to 340° C.

5. A process according to claim 1 wherein said space velocity is 1,500 to 5,000 standard m³ of catalyst per hour.

6. A process according to claim 1 wherein the rate of introduction of said recycle gas is 7.5 to 15 times said space velocity.

7. A process according to claim 1 wherein said total gas load is 10,000 to 25,000 standard m³ per m³ of catalyst per hour.

8. A process according to claim 1 wherein said linear gas flow velocity is from 1.5 to 5 meters per second.

9. A process according to claim 1 wherein said residence time is from 0.05 to 0.5 seconds.

10. A process according to claim 20 wherein said catalyst has an internal surface area of 10 to 100 m² per gram of said catalyst.

11. A process according to claim 20 wherein said catalyst has an iron content of more than 50% by weight.

12. A process according to claim 11 wherein said catalyst contains more than 60% iron by weight.

13. A process according to claim 20 wherein said catalyst contains less than 50% macropores having a diameter of more than about $5 \times 10^{-6}$ to $1 \times 10^{-5}$ cm.

14. A process according to claim 13 wherein said catalyst contains less than 25% of said macropores.

15. A process according to claim 20 wherein said catalyst is in 2 to 5 layers.

16. A process according to claim 20 wherein additional fresh gas is introduced to said gas load downstream.

17. A process according to claim 20 wherein said gas is rich in $H_2$.

18. A process according to claim 20 wherein the ratio of $CO/H_2$ in said gas is at least 1:1.2.

19. A process according to claim 18 wherein said ratio is from 1:1.5 to 1:2.

20. A process according to claim 1 wherein said gas, between entering and leaving reactor, undergoes a temperature increase of from 25° to 100° C.

21. A process according to claim 1 wherein said increase is 30° to 50° C.

* * * * *